United States Patent [19]
Guess et al.

[11] Patent Number: 6,054,455
[45] Date of Patent: Apr. 25, 2000

[54] METHOD FOR TREATING OR PREVENTING CHRONIC NONBACTERIAL PROSTATITIS AND PROSTATODYNIA

[75] Inventors: Harry A. Guess, Chapel Hill, N.C.; Joanne Waldstreicher, Scotch Plains, N.J.; Jay Dee Pearson, Hatfield, Pa.

[73] Assignee: Merck & Co., Inc., Rahway, N.J.

[21] Appl. No.: 09/313,002

[22] Filed: May 17, 1999

Related U.S. Application Data

[60] Provisional application No. 60/085,866, May 15, 1998.
[51] Int. Cl.⁷ ...................... A61K 31/535; A61K 31/445
[52] U.S. Cl. ......................................... 514/231.2; 514/326
[58] Field of Search ................................... 514/326, 231.2

[56] References Cited

U.S. PATENT DOCUMENTS

| | | | |
|---|---|---|---|
| 5,728,815 | 3/1998 | Chung et al. | 530/399 |
| 5,798,363 | 8/1998 | Hagan et al. | 514/299 |
| 5,846,965 | 12/1998 | MacKenzie et al. | 514/210 |
| 5,869,489 | 2/1999 | Shah et al. | 514/253 |

*Primary Examiner*—Raymond Henley, III
*Attorney, Agent, or Firm*—J. Eric Thies; David L. Rose

[57] ABSTRACT

A tachykinin receptor antagonist, in particular a neurokinin-1 receptor antagonist, is useful for the treatment or prevention of chronic nonbacterial prostatitis and/or prostatodynia.

10 Claims, No Drawings

METHOD FOR TREATING OR PREVENTING CHRONIC NONBACTERIAL PROSTATITIS AND PROSTATODYNIA

This application claims priority under 35 USC 119(e) over Provisional Application Ser. No. 60/085,866 filed May 15, 1998.

BACKGROUND OF THE INVENTION

Prostatitis and prostatodynia are extremely prevalent diseases in men (Collins M M, et al., "How common is prostatitis? A national survey of physician visits," *Journal of Urology,* 159:1224–1228 (1998)). There are more outpatient visits for prostatitis than for benign prostatic hypertrophy (BPH) or prostate cancer. Although the epidemiologic evidence is limited, it appears that the prevalence of prostatitis is approximately 2–9% in adult men. It has been suggested that 35–50% of men are affected by prostatitis at some time in life. Based on the National Ambulatory Medical Care Surveys from 1990–1994, approximately 2 million ambulatory visits are made annually for prostatitis. This accounts for 8% of all visits to urologists and 1% of all visits to primary care physicians. Many men remain symptomatic for much of their lives.

This category of poorly understood syndromes is characterized by evidence of prostatic inflammation and by the presence or absence of white blood cells in prostatic fluid and/or pain associated with the prostate. Within this group of syndromes, the origins of chronic idiopathic prostatitis, asymptomatic prostatitis, and prostatodynia are problematic and are probably the least understood. The origin of these diseases have been attributed to some undefinable bacterial or viral infection, but this has never been proven. These syndromes do not exist prior to puberty but have a peak incidence between the ages of 18 and 50. It is possible that these three specific entities actually represent the same disease process in different phases or forms. Suggestions as to the origins of these conditions have included a chemical imbalance in the prostate, infection undetected by current microbiological methods, and autoimmunity to the prostate gland itself.

Chronic nonbacterial prostatitis is an inflammatory and pain condition of unknown etiology characterized by excessive inflammatory cells in prostatic secretions despite no history of documented urinary tract infection and negative bacterial cultures of urine and prostatic secretions. Chronic nonbacterial prostatitis is even more common than bacterial prostatitis. Symptoms simulate those of chronic bacterial prostatitis and these patients usually show an increase in the number of white blood cellss and oval fat bodies in their expressed prostatic secretions. However, they rarely have a history of urinary tract infection, and lower-tract localization cultures fail to reveal a pathogenic organism. Patients with prostatodynia have negative bacterial cultures, normal prostatic secretions, and no history of urinary tract infection. Symptoms of chronic nonbacterial prostatitis and prostatodynia vary but include urinary urgency and frequency, nocturia, dysuria, and pain and discomfort perceived in the pelvic, suprapubic, or genital area. Sometimes postejaculatory pain and discomfort are prominent features. Physical findings for both conditions are nonspecific.

Currently, there are no established treatments for chronic nonbacterial prostatitis or prostatodynia. Antibiotics are often prescribed empirically, but with little evidence of efficacy. Alpha blockers are sometimes prescribed for prostatodynia, but their efficacy has not been established. Patients who respond poorly to medical management or have significant emotional problems are referred for psychiatric intervention. Hot sitz baths and anticholinergic drugs are genearlly employed to provide some symptomatic relief, as is periodic prostatic massage.

Although the present invention is not limited to a specific mechanism of action, the inventors postulate that a neurokinin-1 antagonists would be effective in the treatment of chronic nonbacterial prostatitis or prostatodynia by affecting inflammatory and pain mechanisms in the prostate. In accodance with the present invention, administration of a neurokinin-1 receptor antagonist would reduce both the inflammation and pain that characterize chronic nonbacterial prostatitis and prostatodynia. Furthermore, the effects of the neurokinin-1 receptor antagonist on smooth muscle in the bladder and urethra would also have beneficial effects on the urinary symptoms of prostatitis and prostatodynia. Accordingly, a tacykinin antagonist, in particular a neurokinin-1 receptor antagonist would be useful in the treatment or prevention of chronic nonbacterial prostatitis or prostatodynia.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.,* 1983, 3, 85–141). The NK-1 and NK-2 receptor subtypes are implicated in synaptic transmission (Laneuville et al., *Life Sci.,* 42, 1295–1305 (1988)).

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to SP the known mammalian tachykinins include neurokinin A and neurokinin B. The current nomenclature designates the receptors for substance P, neurokinin A, and neurokinin B as neurokinin-1, neurokinin-2, and neurokinin-3, respectively.

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science,* 199, 1359 (1978); P. Oehme et al., *Science,* 208, 305 (1980)) and plays a role in sensory transmission and pain perception (T. M. Jessell, *Advan. Biochem. Psychopharmacol.* 28 189 (1981)).

Conditions in which substance P has been implicated include disorders of bladder function, such as cystitis, bladder detrusor hyperreflexia, and urinary incontinence (see PCT International Patent Publication No. WO 95/16679 and EPO Patent Publication No. EP 0,610,021). It has been suggested that substance P is implicated in certain urinary tract conditions (Chapple C R, et al., *Journal of Urology,* 146:1637–1644 (1991); Danuser H, et al., *Journal of Urology,* 157:1018–1024 (1997); Palea S, et al., *Journal of Pharmacology and Experimental Therapeutics* 277:700–705 (1996); Tainio H, *Acta. Histochem.,* 97:113–119 (1995)). It has also been suggested that neurokinin-2 receptor antagonists might be useful for treatment of urinary bladder disorders and interstitial cystitis (Palea S, et al., "Pharmacological characterization of tachykinin NK2 receptors on isolated human urinary bladder, prostatic urethra, and prostate," *Journal of Pharmacology and Experimental Therapeutics*, 277:700–705 (1996)). Prior to the present invention, however, it has not been disclosed or suggested that a neurokinin-1 receptor antagonist would be useful for the treatment of chronic nonbacterial prostatitis or prostatodynia. Currently there are only limited means for treating or preventing chronic nonbacterial prostatitis or prostatodynia. In view of the short-comings of existing agents, there is a need for new effective methods for treating or preventing chronic nonbacterial prostatitis or prostatodynia.

SUMMARY OF THE INVENTION

The present invention relates to the use of a tachykinin receptor antagonist, in particular a neurokinin-1 receptor antagonist, for the treatment or prevention of acute or chronic prostatitis, chronic nonbacterial prostatitis and/or prostatodynia comprising the administration of a tachykinin antagonist, in particular a neurokinin-1 receptor antagonist. In a preferred embodiment, the present invention provides a method for treatment or prevention of acute or chronic prostatitis, chronic nonbacterial prostatitis and/or prostatodynia comprising the administration of a neurokinin-1 receptor antagonist.

DESCRIPTION OF THE INVENTION

The present invention is directed to a method for treating or preventing chronic nonbacterial prostatitis in a patient comprising the administration of a tachykinin receptor antagonist, in particular an NK-1 receptor antagonist.

The present invention is directed to a method for treating or preventing acute or chronic prostatitis in a patient comprising the administration of a tachykinin receptor antagonist, in particular an NK-1 receptor antagonist.

The present invention is directed to a method for treating or preventing acute bacterial prostatitis in a patient comprising the administration of a tachykinin receptor antagonist, in particular an NK-1 receptor antagonist.

The present invention is further directed to a method for treating or preventing prostatodynia in a patient comprising the administration of a tachykinin receptor antagonist, in particular an NK-1 receptor antagonist.

The present invention is further directed to a method for ameliorating the symptoms attendant to acute or chronic prostatitis, chronic nonbacterial prostatitis and/or prostatodynia in a patient comprising the administration of a tachykinin receptor antagonist, in particular an NK-1 receptor antagonist.

In a preferred embodiment, the present invention provides a method for treating or preventing acute or chronic prostatitis in a patient comprising the administration of a tachykinin receptor antagonist, in particular an NK-1 receptor antagonist.

In a preferred embodiment, the present invention provides a method for treating or preventing chronic nonbacterial prostatitis in a patient comprising the administration of a tachykinin receptor antagonist, in particular an NK-1 receptor antagonist.

In a preferred embodiment, the present invention provides a method for treating or preventing acute bacterial prostatitis in a patient comprising the administration of a tachykinin receptor antagonist, in particular an NK-1 receptor antagonist.

In a preferred embodiment, the present invention provides a method for treating or preventing prostatodynia in a patient comprising the administration of a tachykinin receptor antagonist, in particular an NK-1 receptor antagonist.

In a preferred embodiment, the present invention further provides a method for ameliorating the symptoms attendant to acute or chronic nonbacterial prostatitis in a patient comprising the administration of a tachykinin receptor antagonist, in particular an NK-1 receptor antagonist.

In a preferred embodiment, the present invention further provides a method for ameliorating the symptoms attendant to acute or chronic prostatitis in a patient comprising the administration of a tachykinin receptor antagonist, in particular an NK-1 receptor antagonist.

In a preferred embodiment, the present invention further provides a method for ameliorating the symptoms attendant to acute bacterial prostatitis in a patient comprising the administration of a tachykinin receptor antagonist, in particular an NK-1 receptor antagonist.

In a preferred embodiment, the present invention further provides a method for ameliorating the symptoms attendant to prostatodynia in a patient comprising the administration of a tachykinin receptor antagonist, in particular an NK-1 receptor antagonist.

The present invention further provides a pharmaceutical composition for treating or preventing acute or chronic prostatitis, chronic nonbacterial prostatitis or prostatodynia in a patient comprising a tachykinin receptor antagonist, in particular an NK-1 receptor antagonist, together with at least one pharmaceutically acceptable carrier or excipient.

The present invention further provides a pharmaceutical composition for ameliorating the symptoms attendant to chronic prostatitis, chronic nonbacterial prostatitis or prostatodynia in a patient comprising a tachykinin receptor antagonist, in particular an NK-1 receptor antagonist, together with at least one pharmaceutically acceptable carrier or excipient.

In accordance with the present invention the tachykinin receptor antagonist is administered to a patient in a quantity sufficient to treat or prevent the symptoms and/or underlying etiology associated with chronic prostatitis, chronic nonbacterial prostatitis or prostatodynia in a patient.

In a further aspect of the present invention, there is provided a pharmaceutical composition for treating or preventing chronic nonbacterial prostatitis in a patient comprising a NK-1 receptor antagonist, together with at least one pharmaceutically acceptable carrier or excipient.

In a further aspect of the present invention, there is provided a pharmaceutical composition ameliorating the symptoms attendant to prostatodynia in a patient comprising a NK-1 receptor antagonist, together with at least one pharmaceutically acceptable carrier or excipient.

The present invention also provides the use of a NK-1 receptor antagonist for the manufacture of a medicament for treating or preventing acute or chronic nonbacterial prostatitis in a patient.

The present invention also provides the use of a NK-1 receptor antagonist for the manufacture of a medicament for treating or preventing prostatodynia in a patient.

The present invention also provides the use of a NK-1 receptor antagonist for the manufacture of a medicament for treating or preventing acute bacterial prostatitis in a patient.

The present invention also provides the use of a NK-1 receptor antagonist for the manufacture of a medicament for ameliorating the symptoms attendant to chronic nonbacterial prostatitis in a patient.

The present invention also provides the use of a NK-1 receptor antagonist for the manufacture of a medicament for ameliorating the symptoms attendant to prostatodynia in a patient.

In an alternate embodiment, the present invention is directed to a method for treating or preventing congestive prostatitis in a patient comprising the administration of a tachykinin receptor antagonist, in particular an NK-1 receptor antagonist.

The present invention is further directed to a method for ameliorating the symptoms attendant to congestive prostatitis in a patient comprising the administration of a tachykinin receptor antagonist, in particular an NK-1 receptor antagonist.

In an alternate embodiment, the present invention is directed to a method for treating or preventing epididymitis, especially congestive epididymitis, in a patient comprising the administration of a tachykinin receptor antagonist, in particular an NK-1 receptor antagonist.

The present invention is further directed to a method for ameliorating the symptoms attendant to epididymitis, especially congestive epididymitis, in a patient comprising the administration of a tachykinin receptor antagonist, in particular an NK-1 receptor antagonist.

In an alternate embodiment, the present invention is directed to a method for treating or preventing post-vasectomy pain and inflammation in a patient comprising the administration of a tachykinin receptor antagonist, in particular an NK-1 receptor antagonist.

The present invention is further directed to a method for ameliorating the symptoms attendant to post-vasectomy pain and inflammation in a patient comprising the administration of a tachykinin receptor antagonist, in particular an NK-1 receptor antagonist.

In an alternate embodiment, the present invention is directed to a method for treating or preventing urethritis in a patient comprising the administration of a tachykinin receptor antagonist, in particular an NK-1 receptor antagonist.

The present invention is further directed to a method for ameliorating the symptoms attendant to urethritis in a patient comprising the administration of a tachykinin receptor antagonist, in particular an NK-1 receptor antagonist.

Although the present invention is useful in any mammal suffering from acute or chronic nonbacterial prostatitis, prostatodynia, congestive prostatitis, epididymitis, post-vasectomy pain and inflammation and/or urethritis, a preferred subject is a human male.

The tachykinin receptor antagonists of use in the present invention may be any tachykinin antagonist known from the art. Preferably, the tachykinin receptor antagonist is a neurokinin-1 (NK-1) or neurokinin-2 (NK-2) receptor antagonist, especially a neurokinin-1 (NK-1) receptor antagonist.

The tachykinin antagonist may be peptidal or non-peptidal in nature, however, the use of a non-peptidal tachykinin receptor antagonist is preferred. In addition, for convenience the use of an orally active tachykinin receptor antagonist is preferred. An especially preferred class of NK-1 receptor antagonist of use in the present invention are those compounds which are orally active and long acting.

Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92120676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

Particularly preferred NK-1 receptor antagonists are those described in PCT International Patent Publication No. WO 95/16679 and European Patent Publication No. 0 577 394 as compounds of formula (I):

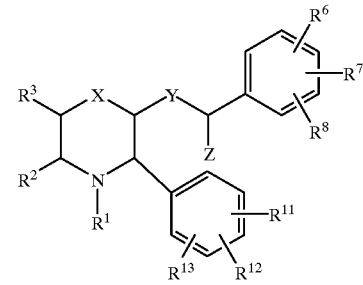

or a pharmaceutically acceptable salt thereof, wherein:
$R^1$ is selected from the group consisting of:
  (1) hydrogen;
  (2) $C_{1-6}$ alkyl, unsubstituted or substituted with one or more of the substituents selected from:
    (a) hydroxy,
    (b) oxo,
    (c) $C_{1-6}$ alkoxy,
    (d) phenyl-$C_{1-3}$ alkoxy,
    (e) phenyl,
    (f) —CN,
    (g) halo, wherein halo is fluoro, chloro, bromo or iodo,
    (h) —NR$^9$R$^{10}$, wherein R$^9$ and R$^{10}$ are independently selected from:

(i) hydrogen,
(ii) $C_{1-6}$ alkyl,
(iii) hydroxy-$C_{1-6}$ alkyl, and
(iv) phenyl,
(i) —$NR^9COR^{10}$,
(j) —$NR^9CO_2R^{10}$,
(k) —$CONR^9R^{10}$,
(l) —$COR^9$,
(m) —$CO_2R^9$,
(n) heterocycle, wherein the heterocycle is selected from the group consisting of:
  (A) benzimidazolyl,
  (B) benzofuranyl,
  (C) benzothiophenyl,
  (D) benzoxazolyl,
  (E) furanyl,
  (F) imidazolyl,
  (G) indolyl,
  (H) isooxazolyl,
  (I) isothiazolyl,
  (J) oxadiazolyl,
  (K) oxazolyl,
  (L) pyrazinyl,
  (M) pyrazolyl,
  (N) pyridyl,
  (O) pyrimidyl,
  (P) pyrrolyl,
  (Q) quinolyl,
  (R) tetrazolyl,
  (S) thiadiazolyl,
  (T) thiazolyl,
  (U) thienyl,
  (V) triazolyl,
  (W) azetidinyl,
  (X) 1,4-dioxanyl,
  (Y) hexahydroazepinyl,
  (Z) piperazinyl,
  (AA) piperidinyl,
  (AB) pyrrolidinyl,
  (AC) tetrahydrofuranyl, and
  (AD) tetrahydrothienyl, and wherein the heterocycle is unsubstituted or substituted with one or more substituent(s) selected from:
    (i) $C_{1-6}$ alkyl, unsubstituted or substituted with halo, —$CF_3$, —$OCH_3$, or phenyl,
    (ii) $C_{1-6}$ alkoxy,
    (iii) oxo,
    (iv) hydroxy,
    (v) thioxo,
    (vi) —$SR^9$,
    (vii) halo,
    (viii) cyano,
    (ix) phenyl,
    (x) trifluoromethyl,
    (xi) —$(CH_2)_m$—$NR^9R^{10}$, wherein m is 0, 1 or 2,
    (xii) —$NR^9COR^{10}$,
    (xiii) —$CONR^9R^{10}$,
    (xiv) —$CO_2R^9$, and
    (xv) —$(CH_2)_m$—$OR^9$;
(3) $C_{2-6}$ alkenyl, unsubstituted or substituted with one or more of the substituent(s) selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$CONR^9R^{10}$,
  (i) —$COR^9$,
  (j) —$CO_2R^9$,
  (k) heterocycle;
(4) $C_{2-6}$ alkynyl;
(5) phenyl, unsubstituted or substituted with one or more of the substituent(s) selected from:
  (a) hydroxy,
  (b) $C_{1-6}$ alkoxy,
  (c) $C_{1-6}$ alkyl,
  (d) $C_{2-5}$ alkenyl,
  (e) halo,
  (f) —CN,
  (g) —$NO_2$,
  (h) —$CF_3$,
  (i) —$(CH_2)_m$—$NR^9R^{10}$,
  (j) —$NR^9COR^{10}$,
  (k) —$NR^9CO_2R^{10}$,
  (l) —$CONR^9R^{10}$,
  (m) —$CO_2NR^9R^{10}$,
  (n) —$COR^9$,
  (o) —$CO_2R^9$;

$R^2$ and $R^3$ are independently selected from the group consisting of:
(1) hydrogen,
(2) $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$NR^9R^{10}$,
  (i) —$NR^9COR^{10}$,
  (j) —$NR^9CO_2R^{10}$,
  (k) —$CONR^9R^{10}$,
  (l) —$COR^9$, and
  (m) —$CO_2R^9$;
(3) $C_{2-6}$ alkenyl, unsubstituted or substituted with one or more of the substituent(s) selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$CONR^9R^{10}$,
  (i) —$COR^9$, and
  (j) —$CO_2R^9$;
(4) $C_{2-6}$ alkynyl;
(5) phenyl, unsubstituted or substituted with one or more of the substituent(s) selected from:
  (a) hydroxy,
  (b) $C_{1-6}$ alkoxy,
  (c) $C_{1-6}$ alkyl,
  (d) $C_{2-5}$ alkenyl,
  (e) halo,
  (f) —CN,
  (g) —$NO_2$,
  (h) —$CF_3$,
  (i) —$(CH_2)_m$—$NR^9R^{10}$,
  (j) —$NR^9COR^{10}$, (k) —NR⁹CO₂R¹⁰,
(l) —CONR⁹R¹⁰,
(m) —CO₂NR⁹R¹⁰,
(n) —COR⁹, and
(o) —CO₂R⁹;

and the groups $R^1$ and $R^2$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) oxazolyl, and
(g) thiazolyl, and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —NR⁹R¹⁰,
(v) halo, and
(vi) trifluoromethyl;

and the groups $R^2$ and $R^3$ may be joined together to form a carbocyclic ring selected from the group consisting of:
(a) cyclopentyl,
(b) cyclohexyl,
(c) phenyl, and wherein the carbocyclic ring is unsubstituted or substituted with one or more substituents selected from:
(i) $C_{1-6}$alkyl,
(ii) $C_{1-6}$alkoxy,
(iii) —NR⁹R¹⁰,
(iv) halo, and
(v) trifluoromethyl;

and the groups $R^2$ and $R^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl, and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —NR⁹R¹⁰,
(v) halo, and
(vi) trifluoromethyl;

$R^6$, $R^7$ and $R^8$ are independently selected from the group consisting of:
(1) hydrogen;
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —NR⁹R¹⁰,
(i) —NR⁹COR¹⁰,
(j) —NR⁹CO₂R¹⁰,
(k) —CONR⁹R¹⁰,
(l) —COR⁹, and
(m) —CO₂R⁹;

(3) $C_{2-6}$ alkenyl, unsubstituted or substituted with one or more of the substituent(s) selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —CONR⁹R¹⁰,
(i) —COR⁹, and
(j) —CO₂R⁹;

(4) $C_{2-6}$ alkynyl;

(5) phenyl, unsubstituted or substituted with one or more of the substituent(s) selected from:
(a) hydroxy,
(b) $C_{1-6}$ alkoxy,
(c) $C_{1-6}$ alkyl,
(d) $C_{2-5}$ alkenyl,
(e) halo,
(f) —CN,
(g) —NO₂,
(h) —CF₃,
(i) —(CH₂)ₘ—NR⁹R¹⁰,
(j) —NR⁹COR¹⁰,
(k) —NR⁹CO₂R¹⁰,
(l) —CONR⁹R¹⁰,
(m) —CO₂NR⁹R¹⁰,
(n) —COR⁹,
(o) —CO₂R⁹;

(6) halo,
(7) —CN,
(8) —CF₃,
(9) —NO₂,
(10) —SR¹⁴, wherein $R^{14}$ is hydrogen or $C_{1-5}$alkyl,
(11) —SOR¹⁴,
(12) —SO₂R¹⁴,
(13) NR⁹COR¹⁰,
(14) CONR⁹COR¹⁰,
(15) NR⁹R¹⁰,
(16) NR⁹CO₂R¹⁰,
(17) hydroxy,
(18) $C_{1-6}$alkoxy,
(19) COR⁹,
(20) CO₂R⁹,
(21) 2-pyridyl,
(22) 3-pyridyl,
(23) 4-pyridyl,
(24) 5-tetrazolyl,
(25) 2-oxazolyl, and
(26) 2-thiazolyl;

$R^{11}$, $R^{12}$ and $R^{13}$ are independently selected from the definitions of $R^6$, $R^7$ and $R^8$;

X is selected from the group consisting of:
(1) —O—,
(2) —S—,
(3) —SO—, and
(4) —SO₂—;

Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein R$^{15}$ and R$^{16}$ are independently selected from the group consisting of:
  (a) C$_{1-6}$ alkyl, unsubstituted or substituted with one or more of the substituents selected from:
    (i) hydroxy,
    (ii) oxo,
    (iii) C$_{1-6}$ alkoxy,
    (iv) phenyl-C$_{1-3}$ alkoxy,
    (v) phenyl,
    (vi) —CN,
    (vii) halo,
    (viii) —NR$^9$R$^{10}$,
    (ix) —NR$^9$COR$^{10}$,
    (x) —NR$^9$CO$_2$R$^{10}$,
    (xi) —CONR$^9$R$^{10}$,
    (xii) —COR$^9$, and
    (xiii) —CO$_2$R$^9$;
  (b) phenyl, unsubstituted or substituted with one or more of the substituent(s) selected from:
    (i) hydroxy,
    (ii) C$_{1-6}$ alkoxy,
    (iii) C$_{1-6}$ alkyl,
    (iv) C$_{2-5}$ alkenyl,
    (v) halo,
    (vi) —CN,
    (vii) —NO$_2$,
    (viii) —CF$_3$,
    (ix) —(CH$_2$)$_m$—NR$^9$R$^{10}$,
    (x) —NR$^9$COR$^{10}$,
    (xi) —NR$^9$CO$_2$R$^{10}$,
    (xii) —CONR$^9$R$^{10}$,
    (xiii) —CO$_2$NR$^9$R$^{10}$,
    (xiv) —COR$^9$, and
    (xv) —CO$_2$R$^9$; and
Z is C$_{1-6}$ alkyl.

Particularly preferred compounds of formula (I) include:
4-(3-(1,2,4-triazolo)methyl)-2(S)-(3,5-bis(trifluoromethyl)benzyloxy)-3(S)-phenyl-morpholine;
4-(3-(1,2,4-triazolo)methyl)-2(S)-(3,5-bis(trifluoromethyl)benzyloxy)-3(R)-phenyl-morpholine;
4-(3-(5-oxo-1H,4H-1,2,4-triazolo)methyl)-2(S)-(3,5-bis(trifluoromethyl)benzyloxy)-3(S)-phenyl-morpholine; and
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; or a pharmaceutically acceptable salt thereof.

An especially preferred compound of formula (I) is
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methylmorpholine; or a pharmaceutically acceptable salt thereof.

Further preferred NK-1 receptor antagonists are those described in PCT International Patent Publication No. WO 95/18124 as compounds of formula (II):

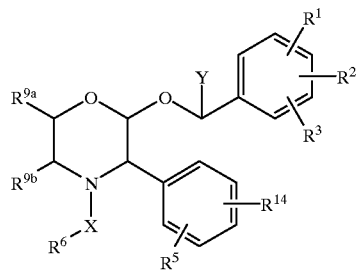

or a pharmaceutically acceptable salt or prodrug thereof, wherein

R$^1$ is hydrogen, halogen, C$_{1-6}$alkyl, C$_{1-6}$alkoxy, CF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;

R$^2$ is hydrogen, halogen, C$_{1-6}$alkyl, C$_{1-6}$alkoxy substituted by C$_{1-4}$alkoxy or CF$_3$;

R$^3$ is hydrogen, halogen or CF$_3$;

R$^4$ is hydrogen, halogen, C$_{1-6}$alkyl, C$_{1-6}$alkoxy, CF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;

R$^5$ is hydrogen, halogen, C$_{1-6}$alkyl, C$_{1-6}$alkoxy substituted by C$_{1-4}$alkoxy or CF$_3$;

R$^6$ is a 5-membered or 6-membered heterocyclic ring containing 2 or 3 nitrogen atoms optionally substituted by =O, =S or a C$_{1-4}$alkyl group, and optionally substituted by a group of the formula ZNR$^7$R$^8$ where Z is C$_{1-6}$alkylene or C$_{3-6}$cycloalkylene;

R$^7$ is hydrogen, C$_{1-4}$alkyl, C$_{3-7}$cycloalkyl or C$_{3-7}$cycloalkylC$_{1-4}$alkyl, or C$_{2-4}$alkyl substituted by C$_{1-4}$alkoxy or hydroxyl;

R$^8$ is hydrogen, C$_{1-4}$alkyl, C$_{3-7}$cycloalkyl or C$_{3-7}$cycloalkylC$_{1-4}$alkyl, or C$_{2-4}$alkyl substituted by one or two substituents selected from C$_{1-4}$alkoxy, hydroxyl or a 4, 5 or 6 membered heteroaliphatic ring containing one or two heteroatoms selected from N, O and S;

or R$^7$, R$^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;

or R$^7$, R$^8$ and the nitrogen atom to which they are attached form a non-aromatic azabicyclic ring system of 6 to 12 ring atoms;

or Z, R$^7$ and the nitrogen atom to which they are attached form a heteroaliphatic ring of 4 to 7 ring atoms which may optionally contain an oxygen ring atom;

R$^{9a}$ and R$^{9b}$ are each independently hydrogen or C$_{1-4}$alkyl, or R$^{9a}$ and R$^{9b}$ are joined so, together with the carbon atoms to which they are attached, there is formed a C$_{5-7}$ ring;

X is an alkylene chain of 1 to 4 carbon atoms optionally substituted by oxo; and Y is a C$_{1-4}$alkyl group optionally substituted by a hydroxyl group; with the proviso that if Y is C$_{1-4}$alkyl, R$^6$ is substituted at least by a group of formula ZNR$^7$R$^8$ as defined above.

Particularly preferred compounds of formula (II) include:

2-(R)-2-(R)-(1-(R)-(3,5-bis(trifluoromethyl)phenyl) ethoxy)-4-(5-(dimethylamino)methyl-1,2,3-triazol-4-yl) methyl-3-(S)-phenylmorpholine;

(1-(R)-(3,5-bis(trifluoromethyl)phenyl)ethoxy)-4-((dimethylamino-methyl)-1,2,3-triazol-4-yl)methyl)-3-(S)-(4-fluorophenyl)morpholine; or a pharmaceutically acceptable salt thereof Further preferred NK-1 receptor antagonists are those described in U.S. Pat. No. 5,691,336 and PCT International Patent Publication No. WO 95/23798 as compounds of formula (III):

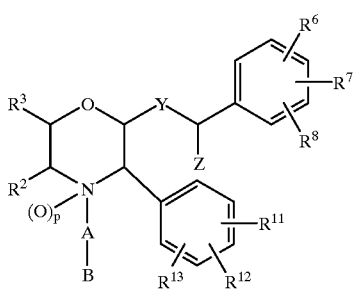

or a pharmaceutically acceptable salt thereof, wherein:

$R^2$ and $R^3$ are independently selected from the group consisting of:

(1) hydrogen, (2) $C_{1-6}$ alkyl, unsubstituted or substituted with one or more of the substituents selected from:
 (a) hydroxy,
 (b) oxo,
 (c) $C_{1-6}$ alkoxy,
 (d) phenyl-$C_{1-3}$ alkoxy,
 (e) phenyl,
 (f) —CN,
 (g) halo,
 (h) —$NR^9R^{10}$, wherein $R^9$ and $R^{10}$ are independently selected from:
  (i) hydrogen,
  (ii) $C_{1-6}$ alkyl,
  (iii) hydroxy-$C_{1-6}$ alkyl, and
  (iv) phenyl,
 (i) —$NR^9COR^{10}$,
 (j) —$NR^9CO_2R^{10}$,
 (k) —$CONR^9R^{10}$,
 (l) —$COR^9$, and
 (m) —$CO_2R^9$;

(3) $C_{2-6}$ alkenyl, unsubstituted or substituted with one or more of the substituent(s) selected from:
 (a) hydroxy,
 (b) oxo,
 (c) $C_{1-6}$ alkoxy,
 (d) phenyl-$C_{1-3}$ alkoxy,
 (e) phenyl,
 (f) —CN,
 (g) halo,
 (h) —$CONR^9R^{10}$,
 (i) —$COR^9$, and
 (j) —$CO_2R^9$;

(4) $C_{2-6}$ alkynyl;

(5) phenyl, unsubstituted or substituted with one or more of the substituent(s) selected from:
 (a) hydroxy,
 (b) $C_{1-6}$ alkoxy,
 (c) $C_{1-6}$ alkyl,
 (d) $C_{2-5}$ alkenyl,
 (e) halo,
 (f) —CN,
 (g) —$NO_2$,
 (h) —$CF_3$,
 (i) —$(CH_2)_m$—$NR^9R^{10}$,
 (j) —$NR^9COR^{10}$,
 (k) —$NR^9CO_2R^{10}$,
 (l) —$CONR^9R^{10}$,
 (m) —$CO_2NR^9R^{10}$,
 (n) —$COR^9$, and
 (o) —$CO_2R^9$;

and, alternatively, the groups $R^2$ and $R^3$ are joined together to form a carbocyclic ring selected from the group consisting of:
 (a) cyclopentyl,
 (b) cyclohexyl,
 (c) phenyl,
 and wherein the carbocyclic ring is unsubstituted or substituted with one or more substituents selected from:
  (i) $C_{1-6}$alkyl,
  (ii) $C_{1-6}$alkoxy,
  (iii) —$NR^9R^{10}$,
  (iv) halo, and
  (v) trifluoromethyl;

and, alternatively, the groups $R^2$ and $R^3$ are joined together to form a heterocyclic ring selected from the group consisting of:
 (a) pyrrolidinyl,
 (b) piperidinyl,
 (c) pyrrolyl,
 (d) pyridinyl,
 (e) imidazolyl,
 (f) furanyl,
 (g) oxazolyl,
 (h) thienyl, and
 (i) thiazolyl,
 and wherein the heterocyclic ring is unsubstituted or substituted with one or more substituent(s) selected from:
  (i) $C_{1-6}$alkyl,
  (ii) oxo,
  (iii) $C_{1-6}$alkoxy,
  (iv) —$NR^9R^{10}$,
  (v) halo, and
  (vi) trifluoromethyl;

$R^6$, $R^7$ and $R^8$ are independently selected from the group consisting of:

(1) hydrogen;

(2) $C_{1-6}$ alkyl, unsubstituted or substituted with one or more of the substituents selected from:
 (a) hydroxy,
 (b) oxo,
 (c) $C_{1-6}$ alkoxy,
 (d) phenyl-$C_{1-3}$ alkoxy,
 (e) phenyl,
 (f) —CN,
 (g) halo,
 (h) —$NR^9R^{10}$,
 (i) —$NR^9COR^{10}$,
 (j) —$NR^9CO_2R^{10}$,
 (k) —$CONR^9R^{10}$,
 (l) —$COR^9$, and
 (m) —$CO_2R^9$;

(3) $C_{2-6}$ alkenyl, unsubstituted or substituted with one or more of the substituent(s) selected from:

(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —CONR$^9$R$^{10}$,
(i) —COR$^9$, and
(j) —CO$_2$R$^9$;

(4) $C_{2-6}$ alkynyl;

(5) phenyl, unsubstituted or substituted with one or more of the substituent(s) selected from:
(a) hydroxy,
(b) $C_{1-6}$ alkoxy,
(c) $C_{1-6}$ alkyl,
(d) $C_{2-5}$ alkenyl,
(e) halo,
(f) —CN,
(g) —NO$_2$,
(h) —CF$_3$,
(i) —(CH$_2$)$_m$—NR$^9$R$^{10}$,
(j) —NR$^9$COR$^{10}$,
(k) —NR$^9$CO$_2$R$^{10}$,
(l) —CONR$^9$R$^{10}$,
(m) —CO$_2$NR$^9$R$^{10}$,
(n) —COR$^9$, and
(o) —CO$_2$R$^9$;

(6) halo,
(7) —CN,
(8) —CF$_3$,
(9) —NO$_2$,
(10) —SR$^{14}$, wherein R$^{14}$ is hydrogen or $C_{1-5}$alkyl,
(11) —SOR$^{14}$
(12) —SO$_2$R$^{14}$,
(13) NR$^9$COR$^{10}$,
(14) CONR$^9$COR$^{10}$,
(15) NR$^9$R$^{10}$,
(16) NR$^9$CO$_2$R$^{10}$,
(17) hydroxy,
(18) $C_{1-6}$alkoxy,
(19) COR$^9$,
(20) CO$_2$R$^9$,
(21) 2-pyridyl,
(22) 3-pyridyl,
(23) 4-pyridyl,
(24) 5-tetrazolyl,
(25) 2-oxazolyl, and
(26) 2-thiazolyl;

R$^{11}$, R$^{12}$ and R$^{13}$ are independently selected from the definitions of R$^6$, R$^7$ and R$^8$, or —OX;

A is selected from the group consisting of:
(1) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —NR$^9$R$^{10}$,
(i) —NR$^9$COR$^{10}$,
(j) —NR$^9$CO$_2$R$^{10}$,
(k) —CONR$^9$R$^{10}$,
(l) —COR$^9$, and
(m) —CO$_2$R$^9$;

(2) $C_{2-6}$ alkenyl, unsubstituted or substituted with one or more of the substituent(s) selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —CONR$^9$R$^{10}$,
(i) —COR$^9$, and
(j) —CO$_2$R$^9$; and (3) $C_{2-6}$ alkynyl;

B is a heterocycle, wherein the heterocycle is selected from the group consisting of:

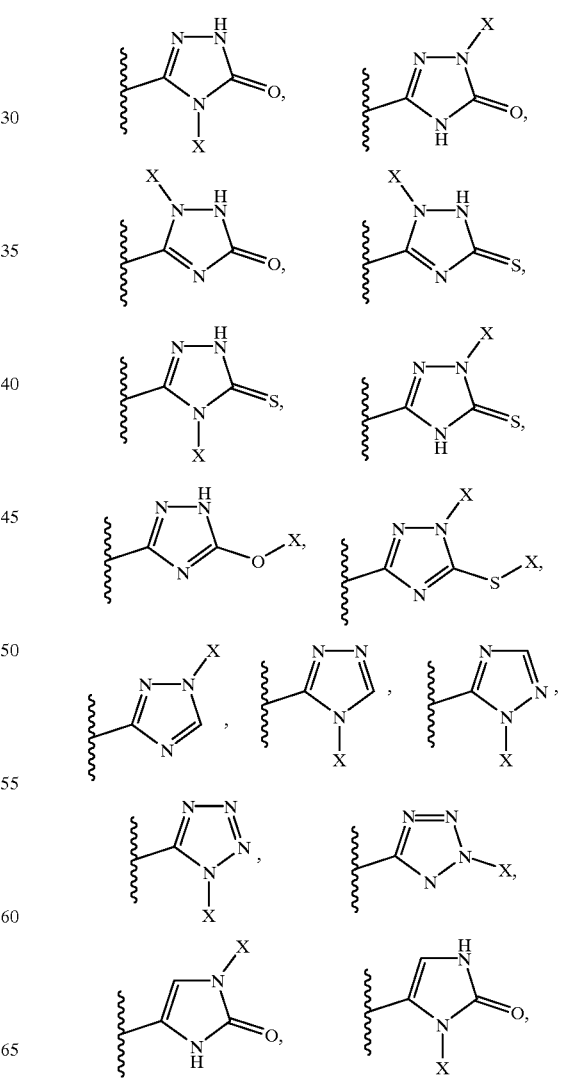

17

-continued

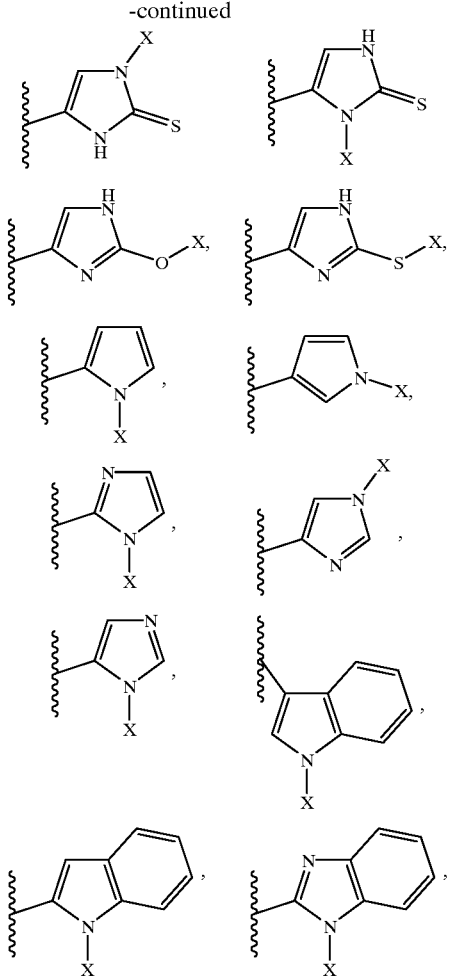

and wherein the heterocycle is substituted in addition to —X with one or more substituent(s) selected from:
(i) hydrogen;
(ii) $C_{1-6}$ alkyl, unsubstituted or substituted with halo, —$CF_3$, —$OCH_3$, or phenyl,
(iii) $C_{1-6}$ alkoxy,
(iv) oxo,
(v) hydroxy,
(vi) thioxo,
(vii) —$SR^9$,
(viii) halo,
(ix) cyano,
(x) phenyl,
(xi) trifluoromethyl,
(xii) —$(CH_2)_m$—$NR^9R^{10}$, wherein m is 0, 1 or 2,
(xiii) —$NR^9COR^{10}$,
(xiv) —$CONR^9R^{10}$,
(xv) —$CO_2R^9$, and
(xvi) —$(CH_2)_m$—$OR^9$;
p is 0 or 1;
X is selected from:
(a) —PO(OH)$O^-$●$M^+$, wherein $M^+$ is a pharmaceutically acceptable monovalent counterion,
(b) —PO($O^-$)$_2$●2$M^+$,
(c) —PO($O^-$)$_2$●$D^{2+}$, wherein $D^{2+}$ is a pharmaceutically acceptable divalent counterion,
(d) —CH($R^4$)—PO(OH)$O^-$●$M^+$, wherein $R^4$ is hydrogen or $C_{1-3}$ alkyl,

18

(e) —CH($R^4$)-PO($O^-$)$_2$●2$M^+$,
(f) —CH($R^4$)-PO($O^-$)$_2$●$D^{2+}$,
(g) —$SO_3^-$●$M+$,
(h) —CH($R^4$)—$SO_3^-$●$M^+$,
(i) —CO—$CH_2CH_2$—$CO_2^-$●$M^+$,
(j) —CH($CH_3$)—O—CO—$R^5$, wherein $R^5$ is selected from the group consisting of:

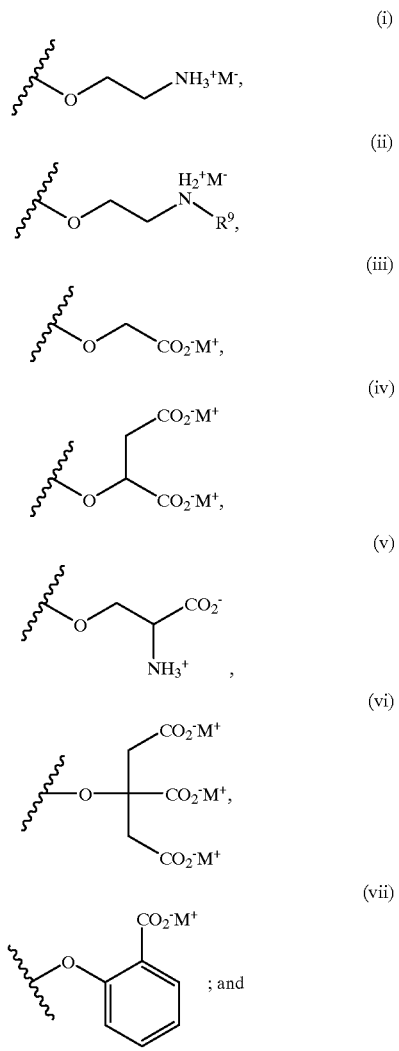

(k) hydrogen, with the proviso that if p is 0 and none of $R^1$, $R^{12}$ or $R^{13}$ are —OX, then X is other than hydrogen;
Y is selected from the group consisting of:
(1) a single bond,
(2) —O—,
(3) —S—,
(4) —CO—,
(5) —$CH_2$—,
(6) —$CHR^{15}$—, and
(7) —$CR^{15}R^{16}$—, wherein $R^{15}$ and $R^{16}$ are independently selected from the group consisting of:
(a) $C_{1-6}$ alkyl, unsubstituted or substituted with one or more of the substituents selected from:
(i) hydroxy,
(ii) oxo, (iii) $C_{1-6}$ alkoxy,
(iv) phenyl-$C_{1-3}$ alkoxy,
(v) phenyl,
(vi) —CN,
(vii) halo,
(viii) —$NR^9R^{10}$,
(ix) —$NR^9COR^{10}$,
(x) —$NR^9CO_2R^{10}$,
(xi) —$CONR^9R^{10}$,
(xii) —$COR^9$, and
(xiii) —$CO_2R^9$;
(b) phenyl, unsubstituted or substituted with one or more of the substituent(s) selected from:
(i) hydroxy,
(ii) $C_{1-6}$ alkoxy,
(iii) $C_{1-6}$ alkyl,
(iv) $C_{2-5}$ alkenyl,
(v) halo,
(vi) —CN,
(vii) —$NO_2$,
(viii) —$CF_3$,
(ix) —$(CH_2)_m$—$NR^9R^{10}$,
(x) —$NR^9COR^{10}$,
(xi) —$NR^9CO_2R^{10}$,
(xii) —$CONR^9R^{10}$,
(xiii) —$CO_2NR^9R^{10}$,
(xiv) —$COR^9$, and
(xv) —$CO_2R^9$;

Z is selected from:
(1) hydrogen,
(2) $C_{1-6}$ alkyl, and
(3) hydroxy, with the proviso that if Y is —O—, Z is other than hydroxy, or if Y is —$CHR^{15}$—, then Z and $R^{15}$ are optionally joined together to form a double bond.

A particularly preferred compound of formula (III) is 2-(R)-(1-(R)-(3,5-bis(trifluoromethyl)phenyl)ethoxy)-3-(S)-(4-fluoro)-phenyl-4-(3-(1-monophosphoryl-5-oxo-1H-1,2,4-triazolo)methyl)morpholine, or a pharmaceutically acceptable salt thereof. In particular, the bis(N-methyl-D-glucamine) salt is preferred.

Further preferred NK-1 receptor antagonists are those described in European Patent Specification No. WO 96/05181, i.e. compounds of formula (IV):

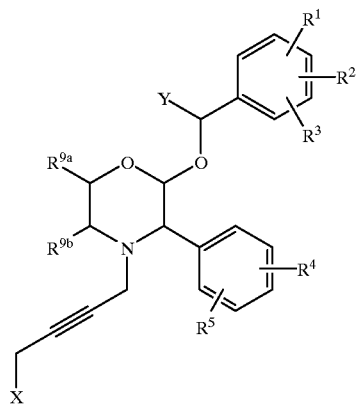

(IV)

wherein:
X is a group of the formula $NR^6R^7$ or a C- or N-linked imidazolyl ring;
Y is hydrogen or $C_{1-4}$alkyl optionally substituted by a hydroxy group;

$R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, $C_{1-6}$alkoxy substituted by $C_{1-4}$alkoxy or $CF_3$;

$R^3$ is hydrogen, halogen or $CF_3$;

$R^4$ is hydrogen, halogen, $C_{1-6}$alkyl, $C_{1-6}$alkoxy, hydroxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, $C_{1-6}$alkoxy substituted by $C_{1-4}$alkoxy or $CF_3$;

$R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

$R^7$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;

or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, S(O) or $S(O)_2$ and which ring may be optionally substituted by one or two groups selected from hydroxy$C_{1-4}$alkyl, $C_{1-4}$alkoxy$C_{1-4}$alkyl, oxo, $COR^a$ or $CO_2R^a$ where $R^a$ is as previously defined;

or $R^6$ and $R^7$ together with the nitrogen atom to which they are attached, form a non-aromatic azabicyclic ring system of 6 to 12 ring atoms;

$R^8$ is hydrogen, $C_{1-4}$alkyl, hydroxy$C_{1-4}$alkyl or $C_{1-4}$alkoxy$C_{1-4}$alkyl; and $R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring; and pharmaceutically acceptable salts thereof.

Specific compounds of formula (IV) of use in the present invention include:
2-(R)-(1-(R)-(3,5-bis(trifluoromethyl)phenyl)ethoxy)-3-(S)-(4-fluorophenyl)-4-(4-morpholinobut-2-yn-yl) morpholine;
2-(R)-(1-(R)-(3,5-bis(trifluoromethyl)phenyl)ethoxy)-4-(4-N,N-dimethylaminobut-2-yn-yl)-3-(S)-(4-fluorophenyl) morpholine;
4-(4-azetidinylbut-2-yn-yl)-2-(R)-(1-(R)-(3,5-bis (trifluoromethyl)phenyl)ethoxy)-3-(S)-(4-fluorophenyl) morpholine;
2-(R)-(1-(R)-(3,5-bis(trifluoromethyl)phenyl)ethoxy)-3-(S)-(4-fluorophenyl)-4-(4-imidazolylbut-2-yn-yl) morpholine;
2-(R)-(1-(R)-(3,5-bis(trifluoromethyl)phenyl)ethoxy)-3-(S)-(4-fluorophenyl)-4-(4-(N-methylpiperazinyl)but-2-yn-yl)morpholine;
4-(4-bis(2-methoxyethyl)aminobut-2-yn-yl)-2-(R)-(1-(R)-(3,5-bis(trifluoromethyl)phenyl)ethoxy)-3-(S)-(4-fluorophenyl)morpholine;
2-(R)-(1-(R)-(3,5-bis(trifluoromethyl)phenyl)ethoxy)-3-(S)-(4-fluorophenyl)-4-(4-pyrrolidinobut-2-yn-yl) morpholine;
3-(S)-(4-fluorophenyl)-2-(R)-(1-(R)-(3-fluoro-5-(trifluoromethyl)phenyl)ethoxy)-4-(4-morpholinobut-2-yn-yl)morpholine;
3-(S)-(4-fluorophenyl)-4-(4-morpholinobut-2-yn-yl)-2-(R)-( 1-(R)-(3-(trifluoromethyl)phenyl)ethoxy) morpholine;

4-(4-azetidinylbut-2-yn-yl)-3-(S)-(4-fluorophenyl)-2-(R)-(1-(R)-(3-(trifluoromethyl)phenyl)ethoxy)morpholine;

2-(R)-(1-(R)-(3,5-bis(trifluoromethyl)phenyl)ethoxy)-4-(4-(N-(2-methoxyethyl)-N-methyl)aminobut-2-yn-yl)-3-(S)-phenylmorpholine;

2-(R)-(1-(R)-(3,5-bis(trifluoromethyl)phenyl)ethoxy)-4-(4-(N-cyclopropyl-N-(2-methoxyethyl)amino)but-2-yn-yl)-3-(S)-phenylmorpholine;

2-(R)-(1-(R)-(3,5-bis(trifluoromethyl)phenyl)ethoxy)-4-(4-(N-isopropyl-N-(2-methoxyethyl)amino)but-2-yn-yl)-3-(S)-phenylmorpholine;

4-(4-(N,N-dimethylamino)but-2-yn-yl)-3-(S)-(4-fluorophenyl)-2-(R)-(1-(S)-(3-fluoro-5-(trifluoromethyl)phenyl-2-hydroxyethoxy)morpholine;

4-(4-azetidinylbut-2yn-yl)-3-(S)-(4-fluorophenyl)-2-(R)-(1-(S)-(3-fluoro-5-(trifluoromethyl)phenyl)-2-hydroxyethoxy)morpholine;

2-(R)-(1-(S)-(3,5-bis(trifluoromethyl)phenyl)-2-hydroxyethoxy)-4-(4-(N,N-dimethylamino)but-2-yn-yl)-3-(S)-(4-fluorophenyl)morpholine;

4-(4-azetidinylbut-2-yn-yl)-2-(R)-(1-(S)-(3,5-bis(trifluoromethyl)phenyl-2-hydroxyethoxy)-3-(S)-(4-fluorophenyl)morpholine;

4-(4-N-bis(2-methoxy)ethyl-N-methylamino)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-(2-(S)-(methoxymethyl)pyrrolidino)but-2-yn-yl)morpholine;

4-(4-(7-azabicyclo[2.2.1]heptano)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-4-(4-diisopropylaminobut-2-yn-yl)-3-(S)-(4-fluorophenyl) morpholine;

2-(R)-(1-(R)-(3-fluoro-5-(trifluoromethyl)phenyl)ethoxy)-4-(4-(2-(S)-(methoxymethyl)pyrrolidino)but-2-yn-yl)-3-(S)-phenylmorpholine;

2-(R)-(1-(R)-(3,5-bis(trifluoromethyl)phenyl)ethoxy)-3-(S)-(4-fluorophenyl)-4-(4-(2-(S)-(hydroxymethyl)pyrrolidino)but-2-yn-yl)morpholine; and pharmaceutically acceptable salts thereof.

Further preferred NK-1 receptor antagonists are those described in European Patent Publication No. 0 436 334 as compounds of formula (V):

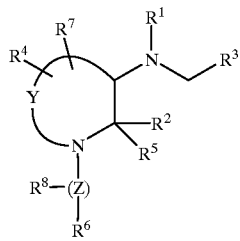

or a pharmaceutically acceptable salt thereof, wherein

Y is $(CH_2)_n$ wherein n is an integer from 1 to 4, and wherein any one of the carbon-carbon single bonds in said $(CH_2)n$ may optionally be replaced by a carbon-carbon double bond, and wherein any one of the carbon atoms of said $(CH_2)n$ may optionally be substituted with $R^4$, and wherein any one of the carbon atoms of said $(CH_2)_n$ may optionally be substituted with $R^7$;

Z is $(CH_2)_m$ wherein m is an integer from 0 to 6, and wherein any one of the carbon-carbon single bonds of $(CH_2)_m$ may optionally be replaced by a carbon-carbon double bond or a carbon-carbon triple bond, and any one of the carbon atoms of said $(CH_2)_m$ may optionally be substituted with $R^8$;

$R^1$ is hydrogen or $C_{1-8}$alkyl optionally substituted with hydroxy, $C_{1-4}$alkoxy or fluoro;

$R^2$ is a radical selected from hydrogen, $C_{1-6}$ straight or branched alkyl, $C_{3-7}$cycloalkyl wherein one of the CH2 groups in said cycloalkyl may optionally be replaced by NH, oxygen or sulphur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$C_{2-6}$alkyl, benzhydryl and benzyl, wherein each of said aryl and heteroaryl groups and the phenyl moieties of said benzyl, phenyl-$C_{2-6}$alkyl and benzhydryl may optionally be substituted with one or more substituents independently selected from halo, nitro, $C_{1-6}$alkyl, $C_{1-6}$alkoxy, trifluoromethyl, amino, $C_{1-6}$alkylamino, $C_{1-6}$alkyl—O—CO, $C_{1-6}$alkyl—O—CO—$C_{1-6}$alkyl, $C_{1-6}$alkyl—CO—O, $C_{1-6}$alkyl—CO—$C_{1-6}$alkyl—O—, $C_{1-6}$alkyl—CO, $C_{1-6}$alkyl—CO—$C_{1-6}$alkyl—, di-$C_{1-6}$alkylamino, —CONH—$C_{1-6}$alkyl, $C_{1-6}$alkyl—CO—NH—$C_{1-6}$alkyl, —NHCOH and —NHCO—$C_{1-6}$alkyl; and wherein one of the phenyl moieties of said benzhydryl may optionally be replaced by naphthyl, thienyl, furyl or pyridyl;

$R^5$ is hydrogen, phenyl or $C_{1-6}$alkyl;

or $R^2$ and $R^5$ together with the carbon to which they are attached, form a saturated ring having from 3 to 7 carbon atoms wherein one of the $CH_2$ groups in said ring may optionally be replaced by oxygen, NH or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of the $(CH_2)$ groups in said cycloalkyl may optionally be replaced by NH, oxygen or sulphur;

wherein each of said aryl and heteroaryl groups may optionally be substituted with one or more substituents, and said $C_{3-7}$cycloalkyl may optionally be substituted with one or two substituents, each of said substituents being independently selected from halo, nitro, $C_{1-6}$alkyl, $C_{1-6}$alkoxy, trifluoromethyl, amino, $C_{1-6}$alkylamino, —CO—NH—$C_{1-6}$alkyl, $C_{1-6}$alkyl—CO—NH—$C_{1-6}$alkyl, —NHCOH and —NH CO—$C_{1-6}$alkyl;

$R^4$ and $R^7$ are each independently selected from hydroxy, halogen, halo, amino, oxo, cyano, methylene, hydroxymethyl, halomethyl, $C_{1-6}$alkylamino, di-$C_{1-6}$alkylamino, $C_{1-6}$alkoxy, $C_{1-6}$alkyl—O—CO, $C_{1-6}$alkyl—O—CO—$C_{1-6}$alkyl, $C_{1-6}$alkyl—CO—O, $C_{1-6}$alkyl—CO—$C_{1-6}$alkyl—O—, $C_{1-6}$alkyl—CO—, $C_{1-6}$alkyl—CO—$C_{1-6}$alkyl, and the radicals set forth in the definition of $R^2$;

$R^6$ is —$NHCOR^9$, —$NHCH_2R^9$, $SO_2R^8$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $C_{1-6}$alkyl, hydrogen, phenyl or phenyl$C_{1-6}$alkyl; with the proviso that (a) when m is O, $R^8$ is absent, (b) when $R^4$, $R^6$, $R^7$ or $R^8$ is as defined in $R^2$, it cannot form together with the carbon to which it is attached, a ring with $R^5$, and (c) when $R^4$ and $R^7$ are attached to the same carbon atom, then either each of $R^4$ and $R^7$ is independently selected from hydrogen, fluoro and $C_{1-6}$alkyl, or $R^4$ and $R^7$, together with the carbon to which they are attached, for a $C_{3-6}$ saturated carbocyclic ring that forms a spiro compound with the nitrogen-containing ring to which they are attached.

A particularly preferred compound of formula (V) is (2S,3S)-cis-3-(2-methoxybenzylamino)-2-phenylpiperidine; or a pharmaceutically acceptable salt thereof.

Another class of NK-1 receptor antagonists is as disclosed in PCT International Patent Publication No. WO 93/21155 as compounds of formula (VI):

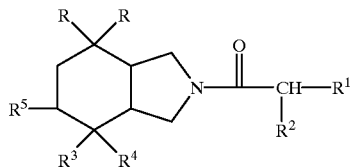

or a pharmaceutically acceptable salt thereof, wherein
radicals R are phenyl radicals optionally 2- or 3-substituted by a halogen atom or a methyl radical;
$R^1$ is optionally substituted phenyl, cyclohexadienyl, naphthyl, indenyl or optionally substituted heterocycle;
$R^2$ is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino;
$R^3$ is optionally 2-substituted phenyl;
$R^4$ is OH or fluorine when $R^5$ is H;
or $R^4$ and $R^5$ are OH;
or $R^4$ and $R^5$ together form a bond.

A particularly preferred compound of formula (VI) is (3aS,4S,7aS)-7,7-diphenyl-4-(2-methoxyphenyl)-2-[(2S)-(2-methoxyphenyl)propionyl]perhydroisoindol-4-ol; or a pharmaceutically acceptable salt thereof.

Another class of NK-1 receptor antagonists of use in the present invention is that described in European Patent Publication No. 0 591 040 as compounds of formula (VII):

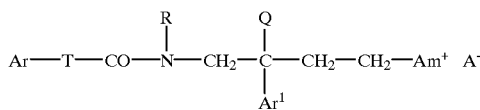

wherein
Ar represents an optionally substituted mono-, di- or tricyclic aromatic or heteroaromatic group;
T represents a bond, a hydroxymethylene group, a $C_{1-4}$alkoxymethylene group or a $C_{1-5}$alkylene group;
Ar' represents a phenyl group which is unsubstituted or substituted by one or more substituents selected from halogen, preferably chlorine or fluorine, trifluoromethyl, $C_{1-4}$alkoxy, $C_{1-4}$alkyl where the said substituents may be the same or different; a thienyl group; a benzothienyl group; a naphthyl group; or an indolyl group;
R represents hydrogen, $C_{1-4}$alkyl, —$C_{1-4}$alkoxy$C_{1-4}$alkyl, or —$C_{2-4}$alkanoyloxy$C_{2-4}$alkyl;
Q represents hydrogen;
or Q and R together form a 1,2-ethylene, 1,3-propylene or 1,4-butylene group;
Am$^+$ represents the radical

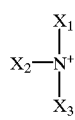

in which $X_1$, $X_2$ and $X_3$, together with the nitrogen atom to which they are attached, form an azabicyclic or azatricyclic ring system optionally substituted by a phenyl or benzyl group; and
A$^-$ represents a pharmaceutically acceptable anion.

A particularly preferred compound of formula (VII) is (+) 1-[2-[3-(3,4-dichlorophenyl)-1-[(3-isopropoxyphenyl)acetyl]-3-piperidinyl]ethyl]-4-phenyl-1-azabicyclo[2,2,2]octane; or a pharmaceutically acceptable salt, especially the chloride, thereof.

Another class of NK-1 receptor antagonists of use in the present invention is that described in European Patent Publication No. 0 532 456 as compounds of formula (VIII):

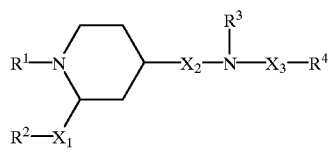

or a pharmaceutically acceptable salt thereof, wherein
$R^1$ represents an optionally substituted aralkyl, aryloxyalkyl, heteroaralkyl, aroyl, heteroaroyl, cycloalkylcarbonyl, aralka noyl, heteroarylalkanoyl, aralkoxycarbonyl or arylcarbamoyl group or the acyl group of an (-amino acid optionally N-substituted by a lower alkanoyl or carbamoyl-lower alkanoyl group;
$R^2$ represents cycloalkyl or an optionally substituted aryl or heteroaryl group;
$R^3$ represents hydrogen, alkyl, carbamoyl or an alkanoyl or alkenoyl group optionally substituted by carboxy or esterified or amidated carboxy;
$R^4$ represents an optionally substituted aryl group or an optionally partially saturated heteroaryl group;
$X_1$ represents methylene, ethylene, a bond, an optionally ketalised carbonyl group or an optionally etherified hydroxymethylene group;
$X_2$ represents alkylene, carbonyl or a bond; and
$X_3$ represents carbonyl, oxo-lower alkyl, oxo(aza)-lower alkyl, or an alkyl group optionally substituted by phenyl, hydroxymethyl, optionally esterified or amidated carboxy, or (in other than the (-position) hydroxy.

A particularly preferred compound of formula (VIII) is (2R*,4S*)-2-benzyl-1-(3,5-dimethylbenzoyl)-N-(4-quinolinylmethyl)-4-piperidineamine; or a pharmaceutically acceptable salt thereof.

Another class of NK-1 receptor antagonists of use in the present invention is that described in European Patent Publication No. 0 443 132 as compounds of formula (IX):

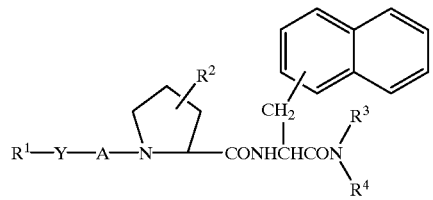

or a pharmaceutically acceptable salt thereof, wherein
wherein $R^1$ is aryl, or a group of the formula:

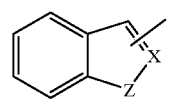

or a pharmaceutically acceptable salt thereof, wherein
X is CH or N; and
Z is O or N—$R^5$, in which $R^5$ is hydrogen or lower alkyl;

$R^2$ is hydroxy or lower alkoxy;

$R^3$ is hydrogen or optionally substituted lower alkyl;

$R^4$ is optionally substituted ar(lower)alkyl;

A is carbonyl or sulfonyl; and

Y is a bond or lower alkenylene.

A particularly preferred compound of formula (IX) is the compound of formula (IXa)

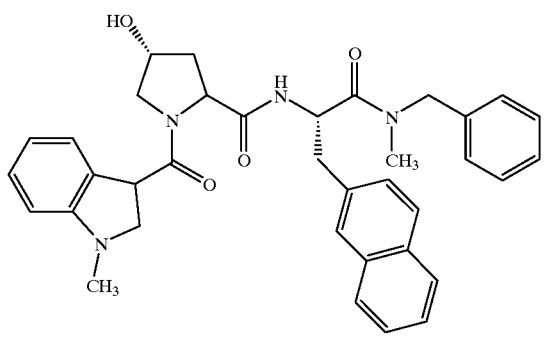

Another class of NK-1 receptor antagonists of use in the present invention is that described in PCT International Patent Publication No. WO 92/17449 as compounds of the formula (X):

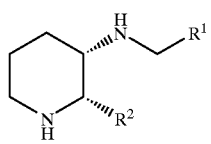

(X)

or a pharmaceutically acceptable salt thereof, wherein $R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $C_{3-7}$cycloalkyl may optionally be substituted with one or two substituents, said substituents being independently selected from chloro, fluoro, bromo, iodo, nitro, $C_{1-10}$alkyl optionally substituted with from one to three fluoro groups, $C_{1-10}$alkoxy optionally substituted with from one to three fluoro groups, amino, $C_{1-10}$alkyl—S—, $C_{1-10}$alkyl—S(O)—, $C_{1-10}$alkyl—SO$_2$—, phenyl, phenoxy, $C_{1-10}$alkyl—SO$_2$NH—, $C_{1-10}$alkyl—SO$_2$NH—$C_{1-10}$alkyl—, $C_{1-10}$alkylamino-di$C_{1-10}$alkyl—, cyano, hydroxy, cycloalkoxy having 3 to 7 carbon atoms, $C_{1-6}$alkylamino, $C_{1-6}$dialkylamino, HC(O)NH— and $C_{1-10}$alkyl—C(O)NH—; and $R^2$ is thienyl, benzhydryl, naphthyl or phenyl optionally substituted with from one to three substituents independently selected from chloro, bromo, fluoro, iodo, cycloalkoxy having 3 to 7 carbon atoms, $C_{1-10}$alkyl optionally substituted with from one to three fluoro groups and $C_{1-10}$alkoxy optionally substituted with from one to three fluoro groups.

A particularly preferred compound of formula (X) is (2S,3S)-3-(2-methoxy-5-trifluoromethoxybenzyl)-amino-2-phenylpiperidine; or a pharmaceutically acceptable salt thereof.

Another class of NK-1 receptor antagonists of use in the present invention is that described in PCT International Patent Publication No. WO 95/08549 as compounds of formula (XI):

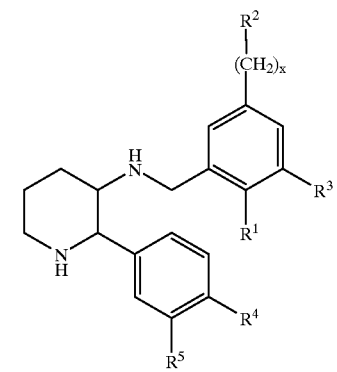

wherein $R^1$ is a $C_{1-4}$alkoxy group;

$R^2$ is

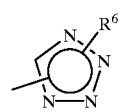

$R^3$ is a hydrogen or halogen atom;

$R^4$ and $R^5$ may each independently represent a hydrogen or halogen atom, or a $C_{1-4}$ alkyl, $C_{1-4}$ alkoxy or trifluoromethyl group;

$R^6$ is a hydrogen atom, a $C_{1-4}$ alkyl, $(CH_2)_m$ cyclopropyl, —S(O)$_n C_{1-4}$ alkyl, phenyl, NR$^7$R$^8$, CH$_2$C(O)CF$_3$ or trifluoromethyl group;

$R^7$ and $R^8$ may each independently represent a hydrogen atom, or a $C_{1-4}$ alkyl or acyl group;

x represents zero or 1;

n represents zero, 1 or 2;

m represents zero or 1;

and pharmaceutically acceptable salts and solvates thereof.

A particularly preferred compound of formula (XI) is [2-methoxy-5-(5-trifluoromethyl-tetrazol-1-yl)-benzyl]-(2S-phenyl-piperidin-3S-yl)-amine; or a pharmaceutically acceptable salt thereof.

Another class of NK-1 receptor antagonists of use in the present invention is that described in PCT International Patent Publication No. WO 97/49710 as compounds of formula (XII):

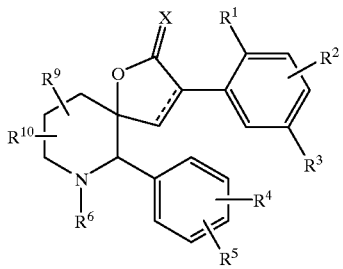

wherein $R^1$, $R^2$, $R^3$, $R^4$, $R^5$, $R^6$, $R^9$, $R^{10}$, and X are as defined therein.

Particularly preferred compounds of formula (XII) are (3S,5R,6S)-3-[2-cyclopropoxy-5-(trifluoromethoxy) phenyl]-6-phenyl-1-oxa-7-aza-spiro[4.5]decane;

(3R,5R,6S)-3-[2-cyclopropoxy-5-(trifluoromethoxy)phenyl]-6-phenyl-1-oxa-7-aza-spiro[4.5]decane; or a pharmaceutically acceptable salt thereof.

Another class of tachykinin receptor antagonists of use in the present invention is that described in PCT International Patent Publication No. WO 95/06645 as compounds of formula (XIII):

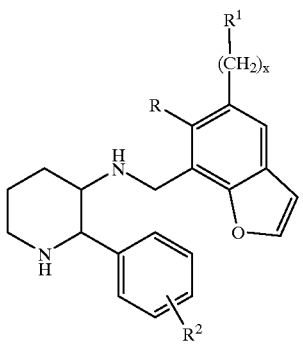

wherein
R represents a hydrogen atom or a $C_{1-4}$ alkoxy group;
$R^1$ is selected from phenyl, optionally substituted by a group —$(CH_2)_n CONR^3 R^4$ or $S(O)_m R^3$; or a 5- or 6-membered aromatic heterocycle containing 1, 2, 3 or 4 heteroatoms selected from oxygen, nitrogen, or sulphur, optionally substituted by a $C_{1-4}$ alkyl, trifluoromethyl or cyano group or a group —$(CH_2)_n CONR^3 R^4$;
$R^2$ represents a hydrogen or halogen atom;
$R^3$ and $R^4$ independently represent hydrogen or $C_{1-4}$ alkyl;
n represents zero, 1 or 2;
m represents zero, 1 or 2;
z represents zero or 1;
and pharmaceutically acceptable salts and solvates thereof A particularly preferred compound of formula (XII) is [5-(5-methyl-tetrazol-1-yl)-benzofuran-7-ylmethyl]-(2S-phenyl-piperidin-3S-yl)-amine; or a pharmaceutically acceptable salt thereof.

Another class of tachykinin receptor antagonists of use in the present invention is that described in PCT International Patent Publication No. WO 95/14017, i.e. compounds of formula (XIV)

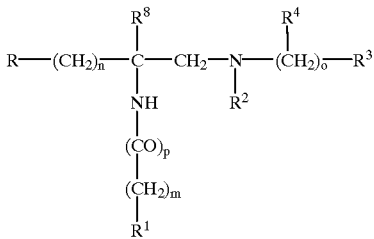

or a pharmaceutically acceptable salt thereof, wherein
m is zero, 1, 2 or 3;
n is zero or 1;
o is zero, 1 or 2;
p is zero or 1;
R is phenyl, 2- or 3-indolyl, 2- or 3-indolinyl, benzothienyl, benzofuranyl, or naphthyl;
which R groups may be substituted with one or two halo, $C_{1-3}$alkoxy, trifluoromethyl, $C_{1-4}$alkyl, phenyl-$C_{1-3}$alkoxy, or $C_{1-4}$alkanoyl groups;

$R^1$ is trityl, phenyl, diphenylmethyl, phenoxy, phenylthio, piperazinyl, piperidinyl, pyrrolidinyl, morpholinyl, indolinyl, indolyl, benzothienyl, hexamethyleneiminyl, benzofuranyl, tetrahydropyridinyl, quinolinyl, isoquinolinyl, reduced quinolinyl, reduced isoquinolinyl, phenyl-($C_{1-4}$alkyl)—, phenyl-($C_{1-4}$alkoxy)—, quinolinyl-($C_{1-4}$alkyl)—, isoquinolinyl-($C_{1-4}$alkyl)—, reduced quinolinyl-($C_{1-4}$alkyl)—, reduced isoquinolinyl-($C_{1-4}$alkyl)-, benzoyl-($C_{1-3}$alkyl)—, $C_{1-4}$alkyl, or 1'NH—$CH_2$—$R^5$;
any one of which $R^1$ groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;
or any one of which $R^1$ groups may be substituted with phenyl, piperazinyl, $C_{3-8}$cycloalkyl, benzyl, $C_{1-4}$alkyl, piperidinyl, pyridinyl, pyrimidinyl, $C_{2-6}$alkanoylamino, pyrrolidinyl, $C_{2-6}$alkanoyl, or $C_{1-4}$alkoxycarbonyl;
any one of which groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;
or $R^1$ is amino, a leaving group, hydrogen, $C_{1-4}$alkylamino, or di($C_{1-4}$alkyl)amino;
$R^5$ is pyridyl, anilino-($C_{1-3}$alkyl)—, or anilinocarbonyl;
$R^2$ is hydrogen, $C_{1-4}$alkyl, $C_{1-4}$alkylsulfonyl, carboxy-($C_{1-3}$alkyl)—, $C_{1-3}$alkoxycarbonyl-($C_{1-3}$alkyl)—, or —CO—$R^6$;
$R^6$ is hydrogen, $C_{1-4}$alkyl, $C_{1-3}$haloalkyl, phenyl, $C_{1-3}$alkoxy, $C_{1-3}$hydroxyalkyl, amino, $C_{1-4}$alkylamino, di($C_{1-4}$alkyl)amino, or —$(CH_2)_q$—$R^7$;
q is zero to 3;
$R^7$ is carboxy, $C_{1-4}$alkoxycarbonyl, $C_{1-4}$alkylcarbonyloxy, amino, $C_{1-4}$alkylamino, di($C_{1-4}$alkyl)amino, $C_{1-6}$alkoxycarbonylamino, or phenoxy, phenylthio, piperazinyl, piperidinyl, pyrrolidinyl, morpholinyl, indolinyl, indolyl, benzothienyl, benzofuranyl, quinolinyl, phenyl-($C_{1-4}$alkyl)—, quinolinyl-($C_{1-4}$alkyl)—, isoquinolinyl-($C_{1-4}$alkyl)—, reduced quinolinyl-($C_{1-4}$alkyl)—, reduced isoquinolinyl-($C_{1-4}$alkyl)—, benzoyl-$C_{1-3}$alkyl;
any one of which aryl or heterocyclic $R^7$ groups may be substituted with halo, trifluoromethyl, $C_{1-4}$alkoxy, $C_{1-4}$alkyl, amino, $C_{1-4}$alkylamino, di($C_{1-4}$alkyl)amino, or $C_{2-4}$alkanoylamino;
or any one of which $R^7$ groups may be substituted with phenyl, piperazinyl, $C_{3-8}$cycloalkyl, benzyl, piperidinyl, pyridinyl, pyrimidinyl, pyrrolidinyl, $C_{2-6}$alkanoyl, or $C_{1-4}$alkoxycarbonyl;
any of which groups may be substituted with halo, trifluoromethyl, amino, $C_{1-4}$alkoxy, $C_{1-4}$alkyl, $C_{1-4}$alkylamino, di($C_{1-4}$alkyl)amino, or $C_{2-4}$alkanoylamino;
$R^8$ is hydrogen or $C_{1-6}$alkyl;
$R^3$ is phenyl, phenyl-($C_{1-6}$alkyl)—, $C_{3-8}$cycloalkyl, $C_{5-8}$cycloalkenyl, $C_{1-8}$alkyl, naphthyl, $C_{2-8}$alkenyl, or hydrogen;
any one or which groups except hydrogen may be substituted with one or two halo, $C_{1-3}$alkoxy, $C_{1-3}$alkylthio, nitro, trifluoromethyl, or $C_{1-3}$alkyl groups; and
$R^4$ is hydrogen or $C_{1-3}$alkyl;
with the proviso that if $R^1$ is hydrogen or halo, $R^3$ is phenyl, phenyl-($C_{1-6}$alkyl)—, $C_{3-8}$cycloalkyl, $C_{5-8}$cycloalkenyl, or naphthyl.

A particularly preferred compound of formula (XIV) is [N-(2-methoxybenzyl)acetylamino]-3-(1H-indol-3-yl)-2-[N-(2-(4-piperidin-1-yl)piperidin-1-yl)acetylamino] propane; or a pharmaceutically acceptable salt thereof.

The preferred compounds of formulae (I), (II), (III) and (IV) will have the 2- and 3-substituents on the morpholine ring in the cis arrangement, the preferred stereochemistry being as shown in the following general formula:

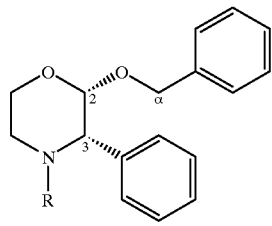

Where the benzyloxy moiety is α-substituted, the preferred stereochemistry of the α-carbon is either (R) when the substituent is an alkyl (e.g. methyl) group or (S) when the substituent is a hydroxyalkyl (e.g. hydroxymethyl) group.

The preparation of the foregoing compounds is fully described in the referenced patents and publications.

Unless otherwise defined herein, suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, sec-butyl and tert-butyl.

Unless otherwise defined herein, suitable alkenyl groups include straight-chained and branched alkenyl groups containing from 2 to 6 carbon atoms. Typical examples include vinyl and allyl groups.

Unless otherwise defined herein, suitable alkynyl groups include straight-chained and branched alkynyl groups containing from 2 to 6 carbon atoms. Typical examples include ethynyl and propargyl groups.

Unless otherwise defined herein, suitable cycloalkyl groups include groups containing from 3 to 7 carbon atoms. Particular cycloalkyl groups are cyclopropyl and cyclohexyl.

Unless otherwise defined herein, suitable aryl groups include phenyl and naphthyl groups. A particular aryl-$C_{1-6}$alkyl, e.g. phenyl-$C_{1-6}$alkyl, group is benzyl.

Unless otherwise defined herein, suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups.

The term "halogen" as used herein includes fluorine, chlorine, bromine and iodine. The compounds of use in this invention may have one or more asymmetric centres and can therefore exist as enantiomers and possibly as diastereoisomers. It is to be understood that the present invention relates to the use of all such isomers and mixtures thereof.

Suitable pharmaceutically acceptable salts of the NK-1 receptor antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

The above compounds are only illustrative of the neurokinin-1 (NK-1) antagonists which are currently under investigation. As this listing of compounds is not meant to be comprehensive, the methods of the present invention may employ any neurokinin-1 receptor antagonist, in particular a neurokinin-1 receptor antagonist which is orally active and long acting. Accordingly, the present invention is not strictly limited to any particular structural class of compound.

Certain of the above defined terms may occur more than once in the above formula and upon such occurrence each term shall be defined independently of the other. Similarly, the use of a particular variable within a noted structural formula is intended to be independent of the use of such variable within a different structural formula.

Full descriptions of the preparation of the tachykinin receptor antagonists which are employed in the present invention may be found in the references cited herein.

The present invention accordingly provides the use of a NK-1 receptor antagonist selected from the compounds of formulae (I), (II), (III), (IV), (V), (VI), (VII), (VIII), (IX), (X), (XI), (XII), (XIII) and (XIV) for the manufacture of a medicament for treating or preventing acute or chronic prostataitis, chronic nonbacterial prostatitis, prostatodynia, congestive prostatitis, epididymitis, post-vasectomy pain and inflammation and/or urethritis, or ameliorating the symptoms attendant to chronic nonbacterial prostatitis, prostatodynia, congestive prostatitis, epididymitis, post-vasectomy pain and inflammation and/or urethritis in a patient.

The present invention also provides a method for treating or preventing acute or chronic prostatitis, chronic nonbacterial prostatitis, prostatodynia, congestive prostatitis, epididymitis, post-vasectomy pain and inflammation and/or urethritis, or ameliorating the symptoms attendant to chronic nonbacterial prostatitis, prostatodynia, congestive prostatitis, epididymitis, post-vasectomy pain and inflammation and/or urethritis, in a patient, which method comprises administration to a patient in need of such treatment an effective amount of a NK-1 receptor antagonist selected from the compounds of formulae (I), (II), (III), (IV), (V), (VI), (VII), (VIII), (IX), (X), (XI), (XII), (XIII) and (XIV).

In a further aspect of the present invention, there is provided a pharmaceutical composition for treating or preventing acute or chronic prostatitis, chronic nonbacterial prostatitis, prostatodynia, congestive prostatitis, epididymitis, post-vasectomy pain and inflammation and/or urethritis, or ameliorating the symptoms attendant to chronic nonbacterial prostatitis, prostatodynia, congestive prostatitis, epididymitis, post-vasectomy pain and inflammation and/or urethritis, in a patient comprising a NK-1 receptor antagonist selected from the compounds of formulae (I), (II), (III), (IV), (V), (VI), (VII), (VIII), (IX), (X), (XI), (XII), (XIII) and (XIV), together with at least one pharmaceutically acceptable carrier or excipient.

The identification of a compound as a tachykinin receptor antagonist, in particular, a neurokinin-1 receptor antagonist, and thus able to have utility in the present invention may be readily determined without undue experimentation by methodology well known in the art.

A tachykinin receptor antagonist may be administered alone or in combination by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Preferably the compositions according to the present invention are in unit dosage forms such as tablets, pills, capsules, powders, granules, solutions or suspensions, or suppositories, for oral, parenteral or rectal administration, by inhalation or insufflation or administration by trans-dermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Preferred compositions for administration by injection include those comprising a NK-1 receptor antagonist as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

Compositions in the form of tablets, pills, capsules or wafers for oral administration are particularly preferred.

It will be known to those skilled in the art that there may be numerous compounds which may be used for treating or preventing chronic prostatitis, chronic nonbacterial prostatitis, prostatodynia, congestive prostatitis, epididymitis, post-vasectomy pain and inflammation and/or urethritis in a patient. Combinations of these therapeutic agents some of which have also been mentioned herein with a tachykinin receptor antagonist will bring additional, complementary, and often synergistic properties to enhance the desirable properties of these various therapeutic agents. In these combinations, the tachykinin receptor antagonist and the therapeutic agents may be independently present in dose ranges from one one-hundredth to one times the dose levels which are effective when these compounds are used singly. In such combination therapy, the tachykinin receptor antagonist may be administered with the other therapeutic agent (e.g., concurrently, concombinantly, sequentially, or in a unitary formulation) such that their therapeutic efficacy overlap.

The tachykinin receptor antagonist may be administered in combination with an alpha blocker, especially an alpha-1a blocker, a 5-alpha reductase inhibitor, a prostate specific antigen conjugate, an antibiotic, in particular a carbapenem antibiotic, anticholinergic agents, a non-steroidal antiinflammatory, a selective cyclooxygenase-2 inhibitor, or a topical urinary analgesic, and the like.

For example, for treating or preventing chronic nonbacterial prostatitis, acute or chronic prostatitis, acute bacterial prostatitis, prostatodynia, congestive prostatitis, epididymitis, post-vasectomy pain and inflammation and/or urethritis in a patient a tachykinin receptor antagonist may be given in combination with such compounds as: an alpha blocker, especially an alpha-1a blocker, such as doxazosin, indoramin, prazosin, tamsulosin, or terazosin; a 5-alpha reductase inhibitor, such as dutasteride or finasteride, especially a type 2 5-alpha reductase inhibitor, a dual 5-alpha reductase inhibitor, or combinations of type 1 and type 2 5-alpha reductase inhibitor; a prostate specific antigen conjugate; an antibiotic, including amikacin, amoxicillin, ampicillin, carbenicillin, cefaclor, cefadroxil, cefamandole, cefazolin, cefoxitin, cephalexin, cephalothin, cephapirin, cephradine, ciprofloxacin, cotrimoxazole, demeclocycline, doxycycline, erythromycin, gentamicin, kanamycin, methenamine hippurate, methenamine mandelate, minocycline, nalidixic acid, nitrofurantoin, norfloxacin, ofloxacin, sulfamethoxazole, sulfonamides, tetracycline, ticarcillin, tobramycin, trimethoprimin, or trimethoprimin-sulfamethoxazole, in particular a carbapenem antibiotic; anticholinergic agents, such as atropine, hyoscyamine, flavoxate, propantheline, or oxybutynin; a non-steroidal antiinflammatory, such as acetomeniphen, alprostadil, asprin, diclofenac, etodolac, ibuprofen, indomethacin, ketoprofe, ketorolac tromethamine, misoprostol, nabumetone, naproxen, naproxen sodium, oxaprozin, piroxicam, spironolactone, spironolactone with hydrochlorothiazide, or trovafloxacin; a corticosteroid; a selective cyclooxygenase-2 inhibitor, such as celecoxib, parecoxib, rofecoxib, valdecoxib, meloxicam, flosulide, nimesulide, MK-663, NS 398, DuP 697, SC-58125, SC-58635, or RS 57067; or a topical urinary analgesic, such as phenazopyridine, and salts thereof, and combinations thereof, and the like, as well as admixtures and combinations thereof.

Typically, the individual daily dosages for these combinations may range from about one-fifth of the minimally recommended clinical dosages to the maximum recommended levels for the entities when they are given singly.

To illustrate these combinations, a tachykinin receptor antagonist effective clinically at a given daily dose range may be effectively combined, at levels which are equal or less than the daily dose range, with the aforementioned compounds. It will be readily apparent to one skilled in the art that the tachykinin receptor antagonist may be employed with other agents for treating or preventing acute or chronic prostatis, chronic nonbacterial prostatitis, prostatodynia, congestive prostatitis, epididymitis, post-vasectomy pain and inflammation and/or urethritis or ameliorating the symptoms attendant to chronic nonbacterial prostatitis, prostatodynia, congestive prostatitis, epididymitis, post-vasectomy pain and inflammation and/or urethritis in a patient.

Naturally, these dose ranges may be adjusted on a unit basis as necessary to permit divided daily dosage and, as noted above, the dose will vary depending on the nature and severity of the disease, weight of patient, special diets and other factors. These combinations may be formulated into pharmaceutical compositions as known in the art and as discussed herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease or disorder, the patient's weight, special diets then being followed by a patient, concurrent medication, the intrinsic tachykinin receptor antagonist activity of the compound, the bioavailability upon oral administration of the compound and other factors which those skilled in the art will recognize.

In the treatment of a condition in accordance with the present invention, an appropriate dosage level will generally be about 0.01 $\mu$g to 50 mg per kg patient body weight per day which may be administered in single or multiple doses. Preferably, the dosage level will be about 0.1 $\mu$g to about 25 mg/kg per day; more preferably about 0.5 $\mu$g to about 10 mg/kg per day. For example, for treating or preventing chronic nonbacterial prostatitis or prostatodynia or ameliorating the symptoms attendant to chronic nonbacterial prostatitis or prostatodynia in a patient, a suitable dosage level is about 0.1 $\mu$g to 25 mg/kg per day, preferably about 0.5 $\mu$g to 10 mg/kg per day, and especially about 1 $\mu$g to 5 mg/kg per day. In larger mammals, for example humans, a typical indicated dose is about 300 $\mu$g to 400 mg orally. A compound may be administered on a regimen of several times per day, for example 1 to 4 times per day, preferably once or twice per day. When using an injectable formulation, a suitable dosage level is about 0.1 $\mu$g to 10 mg/kg per day, preferably about 0.5 $\mu$g to 5 mg/kg per day, and especially about 1 $\mu$g to 1 mg/kg per day. In larger mammals, for example humans, a typical indicated dose is about 100 $\mu$g to 100 mg i.v. A compound may be administered on a regimen of several times per day, for example 1 to 4 times per day, preferably once or twice per day, and more preferably once a day.

Pharmaceutical compositions of the present invention may be provided in a solid dosage formulation preferably comprising about 100 $\mu$g to 500 mg active ingredient, more preferably comprising about 100 $\mu$g to 250 mg active ingredient. The pharmaceutical composition is preferably provided in a solid dosage formulation comprising about 100 $\mu$g, 1 mg, 5 mg, 10 mg, 25 mg, 50 mg, 100 mg, 200 mg or 300 mg active ingredient. A minimum dosage level for the NK-1 receptor antagonist is generally about 5 mg per day, preferably about 10 mg per day and especially about 20 mg per day. A maximum dosage level for the NK-1 receptor antagonist is generally about 1500 mg per day, preferably about 1000 mg per day and especially about 500 mg per day.

It will be appreciated that the amount of the NK-1 receptor antagonist required for use in treating or preventing acute or chronic prostatitis, chronic nonbacterial prostatitis, prostatodynia, congestive prostatitis, epididymitis, post-vasectomy pain and inflammation and/or urethritis or ameliorating the symptoms attendant to chronic nonbacterial prostatitis, prostatodynia, congestive prostatitis, epididymitis, post-vasectomy pain and inflammation and/or urethritis in a patient will vary not only with the particular compounds or compositions selected but also with the route of administration, the nature of the condition being treated, and the age and condition of the patient, and will ultimately be at the discretion of the patient's physician or pharmacist. The length of time during which a tachykinin receptor antagonist will be given varies on an individual basis.

The compounds of formulae (I), (II), (III), (IV), (V), (VI), (VII), (VIII), (IX), (X), (XI), (XII), (XIII) and (XIV) may be prepared by the methods described in EP-A-0 577 394 (or WO 95/16679), WO 95/18124, WO 95/23798, WO 96/05181, EP-A-0 436 334, WO 93/21155, EP-A-0 591 040, EP-A-0 532 456, EP-A-0 443 132, WO 92/17449, WO 95/08549, WO 97/49710, WO 95/06645 and WO 95/14017, respectively.

Particularly preferred NK-1 receptor antagonists of the formulae (I), (II), (III), (IV), (V), (VI), (VII), (VIII), (IX), (X), (XI), (XII), (XIII) and (XIV) for use in the present invention are compounds which are potent NK-1 receptor antagonists, i.e. compounds with an NK-1 receptor affinity ($IC_{50}$) of less than 10 nM.

A particularly preferred class of NK-1 receptor antagonist of use in the present invention are those compounds which are orally active and long acting. The use of this sub-class of NK-1 antagonists for treating or preventing acute or chronic prostatitis, chronic nonbacterial prostatitis, acute bacterial prostatitis, prostatodynia, congestive prostatitis, epididymitis, post-vasectomy pain and inflammation and/or urethritis, especially chronic nonbacterial prostatitis or prostatodynia, or ameliorating the symptoms attendant to chronic nonbacterial prostatitis, prostatodynia, congestive prostatitis, epididymitis, post-vasectomy pain and inflammation and/or urethritis, especially chronic nonbacterial prostatitis or prostatodynia, in a patient represents a further aspect of the present invention.

Thus, the present invention provides the use of an NK-1 receptor antagonist in an oral, once-a-day medicament for treating or preventing acute or chronic prostatitis, chronic nonbacterial prostatitis, acute bacterial prostatitis, prostatodynia, congestive prostatitis, epididymitis, post-vasectomy pain and inflammation and/or urethritis, especally chronic nonbacterial prostatitis or prostatodynia, or ameliorating the symptoms attendant to chronic nonbacterial prostatitis, acute bacterial prostatitis, prostatodynia, congestive prostatitis, epididymitis, post-vasectomy pain and inflammation and/or urethritis, especially chronic nonbacterial prostatitis or prostatodynia, in a patient. The compounds of this class exhibit advantageous benefits when compared against conventional methods for treating or preventing chronic nonbacterial prostatitis, prostatodynia, congestive prostatitis, epididymitis, post-vasectomy pain and inflammation and/or urethritis, in a patient.

In particular, the present invention provides a means for the identification of NK-1 receptor antagonists which would be especially effective in an oral once-a-day medicament for treating or preventing acute or chronic prostatitis, chronic nonbacterial prostatitis, acute bacterial prostatitis, prostatodynia, congestive prostatitis, epididymitis, post-vasectomy pain and inflammation and/or urethritis or ameliorating the symptoms attendant to chronic nonbacterial prostatitis, acute bacterial prostatitis, prostatodynia, congestive prostatitis, epididymitis, post-vasectomy pain and inflammation and/or urethritis in a patient.

Furthermore, the exceptional pharmacology of the class of NK-1 receptor antagonists of use in the present invention results in a rapid onset of action.

The present invention accordingly provides the use of an orally active, long acting NK-1 receptor antagonist (as hereinafter defined) for the manufacture of a medicament adapted for oral administration for treating or preventing acute or chronic prostatitis, chronic nonbacterial prostatitis, acute bacterial prostatitis, prostatodynia, congestive prostatitis, epididymitis, post-vasectomy pain and inflammation and/or urethritis or ameliorating the symptoms attendant to chronic nonbacterial prostatitis, prostatodynia, congestive prostatitis, epididymitis, post-vasectomy pain and inflammation and/or urethritis in a patient.

The present invention also provides a method for treating or preventing acute or chronic prostatitis, chronic nonbacterial prostatitis, acute bacterial prostatitis, prostatodynia, congestive prostatitis, epididymitis, post-vasectomy pain and inflammation and/or urethritis or ameliorating the symptoms attendant to chronic nonbacterial prostatitis, prostatodynia, congestive prostatitis, epididymitis, post-vasectomy pain and inflammation and/or urethritis in a patient, which method comprises the oral administration to a patient in need of such treatment of an effective amount of an orally active, long acting NK-1 receptor antagonist (as defined herein).

In a further aspect of the present invention, there is provided an oral pharmaceutical composition for treating or preventing acute or chronic prostatitis, chronic nonbacterial prostatitis, acute bacterial prostatitis, prostatodynia, congestive prostatitis, epididymitis, post-vasectomy pain and inflammation and/or urethritis or ameliorating the symptoms attendant tochronic nonbacterial prostatitis, prostatodynia, congestive prostatitis, epididymitis, post-vasectomy pain and inflammation and/or urethritis in a patient which comprises an orally active, long acting NK-1 receptor antagonist (as hereinafter defined), together with a pharmaceutically acceptable carrier or excipient.

It will be appreciated to those skilled in the art that reference herein to treatment extends to prophylaxis (prevention) as well as the treatment of the noted diseases/disorders and symptoms. Because the specific diagnosis of chronic nonbacterial prostatitis or prostatodynia in a particular patient may be difficult, the patient may benefit from the prophylactic administration of a subject compound in accordance with the present invention.

Preferred NK-1 receptor antagonists for use in the present invention as orally active, long acting, CNS-penetrant NK-1 receptor antagonists are selected from the classes of compounds described in European Patent Specification No. 0 577 394, and International Patent Specification Nos. 95/08549, 95/18124, 95/23798, 96/05181 and WO 97/49710.

Thus, further particularly preferred NK-1 receptor antagonists of use in the present invention include:

(±)-(2R3R,2S3S)-N-{[2-cyclopropoxy-5-(trifluoromethoxy)phenyl]methyl}-2-phenylpiperidin-3-amine;

2-(S)-(3,5-bis(trifluoromethyl)benzyloxy)-3(S)-(4-fluorophenyl)-4-(3-(5-oxo-1H,4H-1,2,4-triazolo)methyl) morpholine;

2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;

2-(S)-(3,5-bis(trifluoromethyl)benzyloxy)-4-(3-(5-oxo-1H,4H-1,2,4-triazolo)methyl)-3-(S)-phenyl-morpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo) methyl)morpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

(3S,5R,6S)-3-[2-cyclopropoxy-5-(trifluoromethoxy) phenyl]-6-phenyl-1-oxa-7-aza-spiro[4.5]decane;

(3R,5R,6S)-3-[2-cyclopropoxy-5-(trifluoromethoxy) phenyl]-6-phenyl-1-oxa-7-aza-spiro[4.5]decane;

2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl) morpholine; or a pharmaceutically acceptable salt thereof.

Full descriptions of the preparation of the tachykinin receptor antagonists which may be employed in the present invention may be found in the references cited herein.

The following examples are provided for the purpose of further illustration only and are not intended to be limitations on the disclosed invention.

EXAMPLE 1

NK-1 Receptor binding Assay

NK-1 receptor binding assays are performed in intact Chinese hamster ovary (CHO) cells expressing the human NK-1 receptor using a modification of the assay conditions described by Cascieri et al, *J. Pharmacol. Exp. Ther.*, 1992, 42, 458. Typically, the receptor is expressed at a level of $3 \times 10^5$ receptors per cell. Cells are grown in monolayer culture, detached from the plate with enzyme-free dissociation solution (Speciality Media Inc.), and washed prior to use in the assay. $^{125}$I-Tyr$^8$-substance P (0.1 nM, 2000 Ci/mmol; New England Nuclear) is incubated in the presence or absence of test compounds (dissolved in 5 µl dimethylsulphoxide, DMSO) with $5 \times 10^4$ CHO cells. Ligand binding is performed in 0.25 ml of 50 mM Tris-HCl, pH7.5, containing 5 mM $MnCl_2$, 150 mM NaCl, 0.02% bovine serum albumin (Sigma), 50 µg/ml chymostatin (Peninsula), 0.1 nM phenylmethylsulphonyl fluoride, 2 µg/ml pepstatin, 2 µg/ml leupeptin and 2.8 µg/ml furoyl saccharine. The incubation proceeds at room temperature until equilibrium is achieved (>40 minutes) and the receptor-ligand complex is harvested by filtration over GF/C filters pre-soaked in 0.1% polyethylenimine using a Tomtek 96-well harvester. Non-specific binding is determined using excess substance P (1 µM) and represents <10% of total binding.

Particularly preferred NK-1 receptor antagonists of use in the present invention are compounds which are potent NK-1 receptor antagonists, i.e. compounds with an NK-1 receptor affinity ($IC_{50}$) of less than 10 nM, favourably less than 2 nM and preferably less than 1 nM.

The following examples illustrate pharmaceutical compositions according to the invention.

EXAMPLE 2
Tablet formulation containing 50–300 mg of NK-1 antagonist

|  | Amount mg | | |
|---|---|---|---|
| NK-1 antagonist | 50.0 | 100.0 | 300.0 |
| Microcrystalline cellulose | 80.0 | 80.0 | 80.0 |
| Modified food corn starch | 80.0 | 80.0 | 80.0 |
| Lactose | 189.5 | 139.5 | 439.5 |
| Magnesium Stearate | 0.5 | 0.5 | 0.5 |

The active ingredient, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the NK-1 receptor antagonist per tablet.

EXAMPLE 3
Parenteral injection formulation

|  | Amount |
|---|---|
| Active Ingredient | 10 to 300 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient is dissolved or suspended in the solution and made up to volume.

EXAMPLE 4

Double-Blind, Placebo-Controlled Study to Determine the Effect of a Substance P Antagonist on Patients Suffering from Chronic Nonbacterial Prostatitis Approximately twenty patients diagnosed as suffering from chronic nonbacterial prostatitis receive either the substance P receptor antagonist 2-(R)-(1-(R)-(3,5-bis (trifluoromethyl)-phenyl)-ethoxy)-3-(S)-(4-fluoro-phenyl)-4-(3-(5-oxo-1H,4H-1,2,4-triazolo)methyl-morpholine (30 mg/day) or a placebo. Each subject participates in 6 randomized test periods; in 3 of the test periods, each is given the substance P antagonist and in the other 3 test periods, is given a placebo. Efficacy of the test compound is assessed by reference to immunological profile, rating scales, checklists and diminishment of the attendant disease state. The results of the foregoing study would indicate that the administration of a substance P antagonist would be expected to have a positive effect with respect to placebo in the treatment or prevention of chronic nonbacterial prostatitis following drug treatment.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for the treatment or prevention of chronic nonbacterial prostatitis in a patient which comprises administering an effective amount of a tachykinin receptor antagonist.

2. The method of claim 1 wherein the tachykinin receptor antagonist is a neurokinin-1 receptor antagonist.

3. The method of claim 2 wherein the neurokinin-1 receptor antagonist is an orally active neurokinin-1 receptor antagonist.

4. The method of claim 3 wherein the neurokinin-1 receptor antagonist possesses a long duration of action.

5. The method of claim 1 wherein the tachykinin antagonist is employed in conjunction with an agent selected from the group consisting of: alpha-1a blockers, 5-alpha reductase inhibitors, anticholinergic agents, carbapenem antibiotics, selective cyclooxygenase-2 inhibitors, prostate specific antigen conjugates, non-steroidal antiinflammatories, and topical urinary analgesics.

6. A method for the treatment or prevention of prostatodynia in a patient which comprises administering an effective amount of a tachykinin receptor antagonist.

7. The method of claim 6 wherein the tachykinin receptor antagonist is a neurokinin-1 receptor antagonist.

8. The method of claim 7 wherein the neurokinin-1 receptor antagonist is an orally active neurokinin-1 receptor antagonist.

9. The method of claim 8 wherein the neurokinin-1 receptor antagonist possesses a long duration of action.

10. The method of claim 6 wherein the tachykinin antagonist is employed in conjunction with an agent selected from the group consisting of: alpha-1a blockers, 5-alpha reductase inhibitors, anticholinergic agents, carbapenem antibiotics, selective cyclooxygenase-2 inhibitors, prostate specific antigen conjugates, non-steroidal antiinflammatories, and topical urinary analgesics.

* * * * *